_United States Patent_ [19]

Hass

[11] Patent Number: 4,876,658

[45] Date of Patent: Oct. 24, 1989

[54] METHOD AND APPARATUS FOR SYSTEMATICALLY TESTING OBJECTS INCLUDING TENNIS BALLS

[75] Inventor: Hyman Hass, Stamford, Conn.

[73] Assignees: United States Tennis Association Incorporated, New York; Allard Avionics Corp., Freeport, both of N.Y.

[21] Appl. No.: 897,942

[22] Filed: Aug. 19, 1986

[51] Int. Cl.[4] ............... G06F 15/20; A63B 37/00; G01N 3/08; B07C 5/00

[52] U.S. Cl. .................... 364/550; 364/478; 364/552; 73/13; 73/45.1; 73/866; 209/555; 209/699; 273/61 R

[58] Field of Search ............ 364/473, 478, 468, 550, 364/551, 552; 73/7, 78, 37.6, 45.1, 49.4, 146, 861.91, 863, 865.8, 866, 13, 79, 147, 105, 760; 33/178; 209/538, 555, 556, 699; 273/61 D, 61 R

[56] References Cited

U.S. PATENT DOCUMENTS

| | | | |
|---|---|---|---|
| 3,435,685 | 4/1969 | Watkin et al. | 73/863.91 |
| 3,515,053 | 6/1970 | Mylin | 73/863 |
| 4,004,693 | 1/1977 | Tsuji et al. | 209/555 |
| 4,006,626 | 2/1977 | Ruzicka et al. | 73/13 |
| 4,114,350 | 9/1978 | Snyder | 73/78 X |
| 4,148,213 | 4/1979 | Prakken | 209/699 X |
| 4,154,095 | 5/1979 | Snyder | 73/78 |
| 4,472,960 | 9/1984 | Motoyama et al. | 73/7 |
| 4,509,362 | 4/1985 | Lyons | 73/13 X |
| 4,511,044 | 4/1985 | Connor et al. | 364/552 X |
| 4,555,028 | 11/1985 | Valehrach | 73/78 X |
| 4,649,503 | 3/1987 | Keller | 364/473 X |
| 4,687,107 | 8/1987 | Brown et al. | 209/556 |
| 4,691,830 | 9/1987 | Ahl et al. | 209/555 |
| 4,704,900 | 10/1987 | Beebe | 73/146 |

FOREIGN PATENT DOCUMENTS 1167465  7/1985  U.S.S.R. ................ 73/45.1

_Primary Examiner_—Parshotam S. Lall
_Assistant Examiner_—Joseph L. Dixon
_Attorney, Agent, or Firm_—Pennie & Edmonds

[57] ABSTRACT

A computer-controlled object testing and measuring apparatus having a plurality of stations including a control center for initiating, controlling and terminating each procedure at each station. The control center also controls transport and handling of the objects such as tennis balls, between and at the stations. The plurality of computer controlled test and measuring stations initially condition objects and then test and measure such objects in a controlled and timed manner in a selected sequence. Data is gathered, recorded, processed and stored.

7 Claims, 20 Drawing Sheets

CONCURRENT TESTING CHART

| BALL | TEST CYCLE → | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| 1 | X | Y | Z | X | Y | Z | X | Y | Z | A | G | N | W | | | | | | B | F | I" | R | F | I" | R | F | I" | R | I" | R | R |
| 2 | | X | Y | Z | X | Y | Z | X | Y | Z | A | G | N | W | | | | | | | F | I" | R | F | I" | R | F | I" | R | I" | R |
| 3 | | | X | Y | Z | X | Y | Z | X | Y | Z | A | G | N | W | | | | | B | | F | I" | F | R | R | I" | R | F | I" | F |
| 4 | | | | Y | Z | X | Y | Z | X | Y | Z | A | G | N | W | | | | | G | N | W | | R | F | B | B | R | F | I" | F |
| 5 | | | | | X | Y | Z | X | Y | Z | X | Y | Z | X | Y | Z | Y | Z | A | A | G | N | W | | | | | | | |
| 6 | | | | | | X | Y | Z | X | Y | Z | Y | Z | X | Y | Z | Z | X | N | Z | A | G | N | W | | | B | B | F | |
| 7 | | | | | | | | | X | Y | Z | X | Y | Z | Y | Z | Y | Y | Y | Y | X | X | Y | Y | Y | Y | | | | |
| 8 | | | | | | | | | | | | X | Y | Z | X | Y | X | X | X | X | Y | Y | X | X | X | X | X | Z | G | N |
| 9 | | | | | | | | | | | | | | | | | Y | Y | | Z | Z | Z | Z | Z | Z | Z | Y | Y | Y | A |
| 10 | | | | | | | | | | | | | | | | | | | | | X | X | Y | X | Y | N | Z | Y | N | Z |
| 11 | | | | | | | | | | | | | | | | | | | | | | | Z | X | X | Z | X | X | X | |
| 12 | | | | | | | | | | | | | | | | | | | | | | | | | | | | | | |

PRE COMPRESSION: X, Y, Z
SIZE: A = Actual, G = Go, N = No/Go
WEIGHT: W
BOUNCE: B
DEFORMATION: F = Forward, I" = 1" Deformation, R = Reverse

METHOD AND APPARATUS FOR SYSTEMATICALLY TESTING OBJECTS INCLUDING TENNIS BALLS

BACKGROUND OF THE INVENTION

Tennis balls and other objects have heretofore been measured, tested, and otherwise treated to determine if they meet standards or specifications (see U.S. Pat. No. 4,472,960). In particular, tennis balls have been tested using test stations in which operation of the stations is by hand and transport of the balls from station-to-station is manually accomplished. Testing is formed to meet ball requirements of international, national and other tennis organizations.

Prior ball testing equipment has included calipers, "go no-go" gauges for measuring diameters, and scales for determining weight. Other ball test equipment has included compression vices for compressing the ball under known loads to measure ball deflection.

While other semiautomated systems for transport and inspection have been proposed for meat packages (U.S. Pat. No. 3,515,053) and biscuits (U.S. Pat. No. 3,435,685) no satisfactory system or method for testing objects, such as tennis balls, has been known or available.

SUMMARY OF THE INVENTION

Broadly, the present invention is a computer-controlled array of conditioning, test and measuring stations for conditioning objects and thereafter testing and measuring the objects in a controlled, timed, and selected sequence. A central computer initiates, controls and terminates each test step at each substation in each test station. The computer also controls the electromechanical devices which transport and handle the objects and finally the computer processes test information and inputs such information in processed form to a display terminal and to a printer to record selected measurements and other test results.

It is a feature that a plurality of deformable objects such as tennis balls may concurrently be conditioned, tested and measured while test data is recorded, processed and stored.

BRIEF DESCRIPTION OF THE DRAWINGS

FIG. 9 is a sectional end view showing the ball detectors;
FIG 12 depicts a testing chart for a ten-ball, thirty cycle test.

DESCRIPTION OF THE PREFERRED EMBODIMENTS

Figure 1:
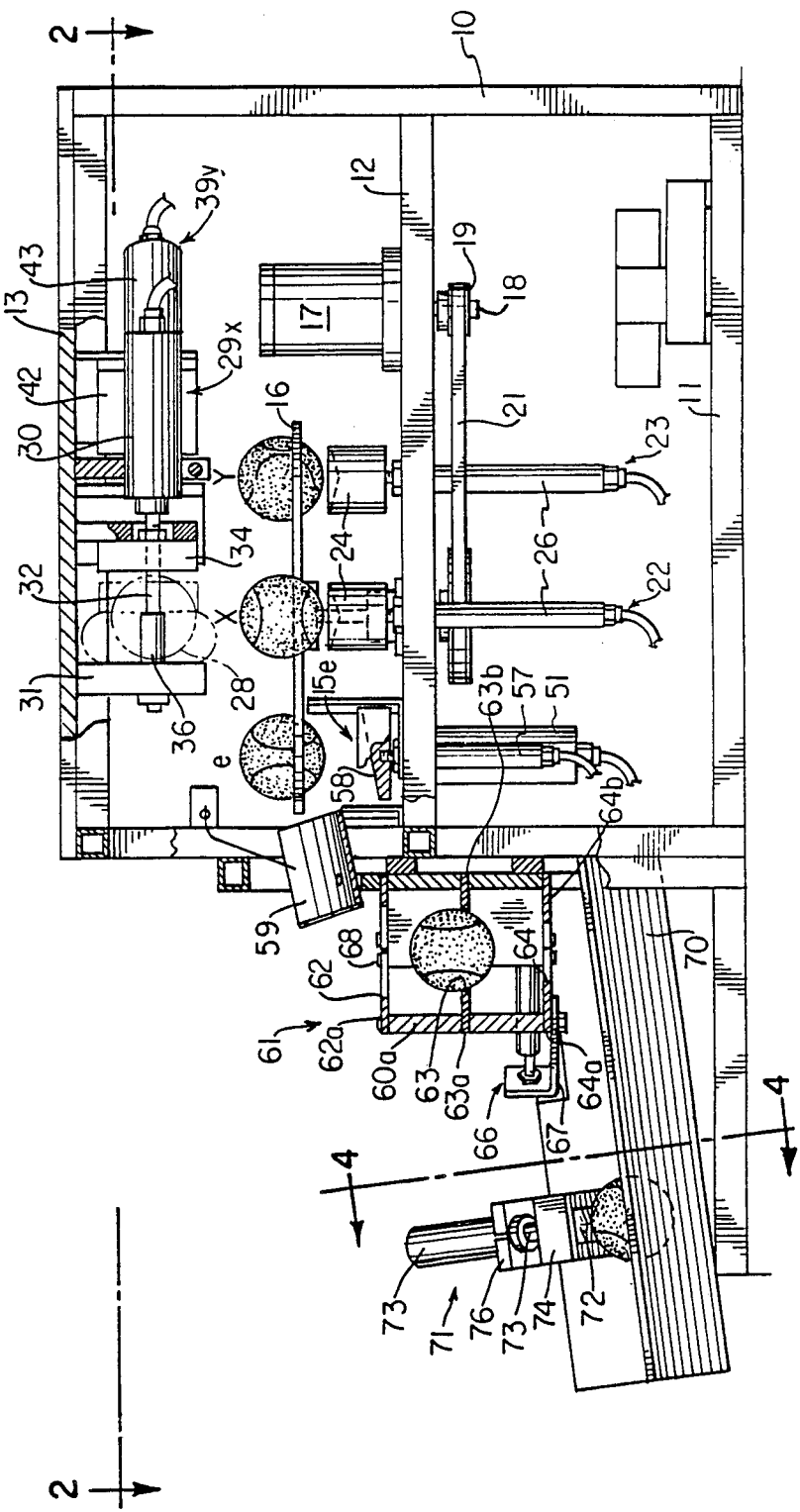
FIG. 1 is an elevational view of the preconditioning and sizing stations.
Figure 1A:
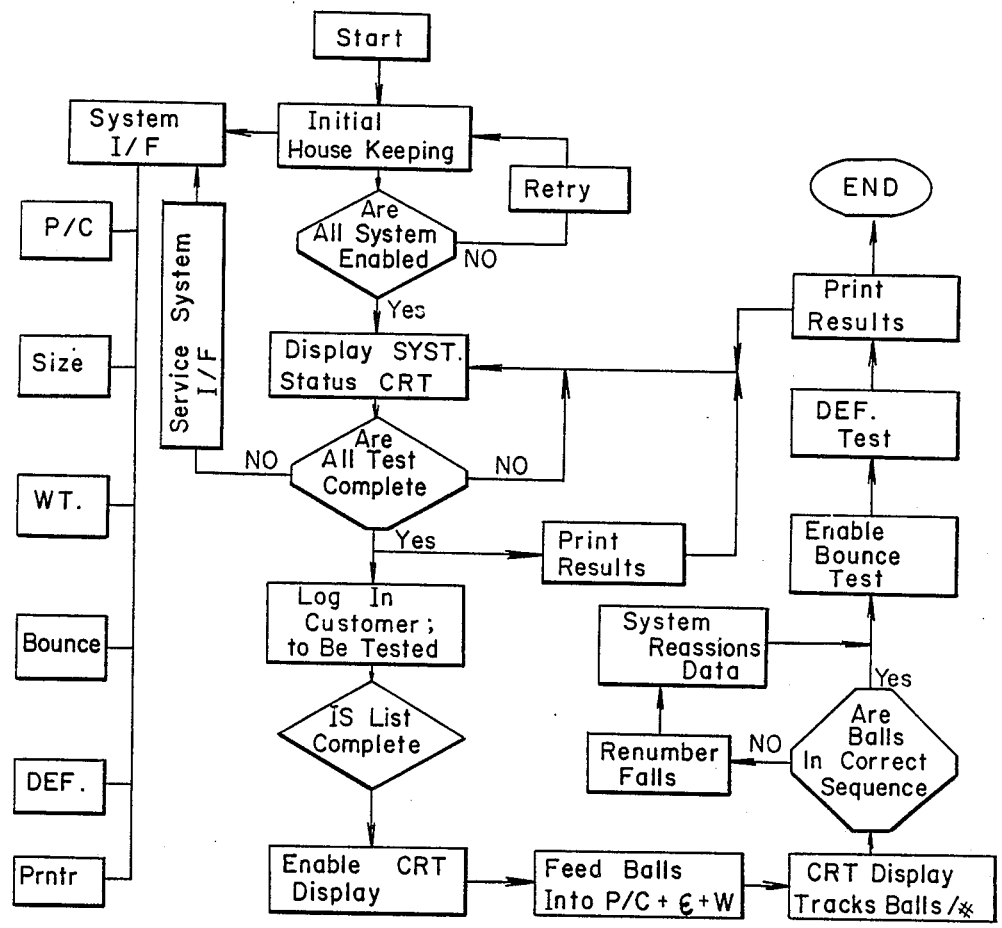
FIG. 1A is a flow sheet showing the overall method.

With respect to FIG. 1A the components of the system steps to be followed to practice of the invention are shown in diagram form. The system is prepared for start up including entering data identifying the plurality of balls to be tested by customer name, by individual ball, and so forth. Balls are fed seriatim to the first station for preconditioning. The video display is used to assure proper sequence and operation of the system. Upon completion of the bounce test, the balls are again fed in proper order to the final station for the deformation tests. Finally, tests may be printed for reporting to the customer.

Figure 1B:
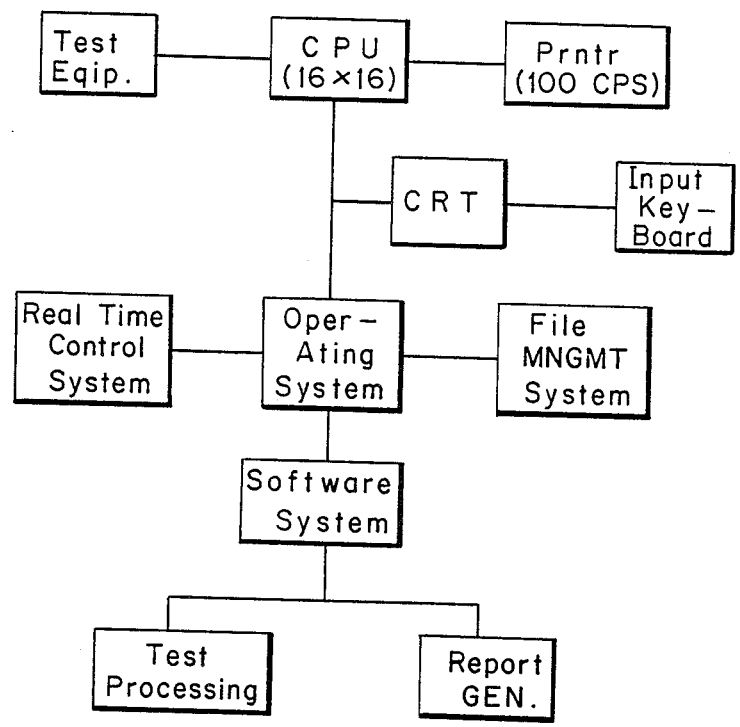
FIG. 1B is a block diagram relating to the method of the invention.
Figure 1C:
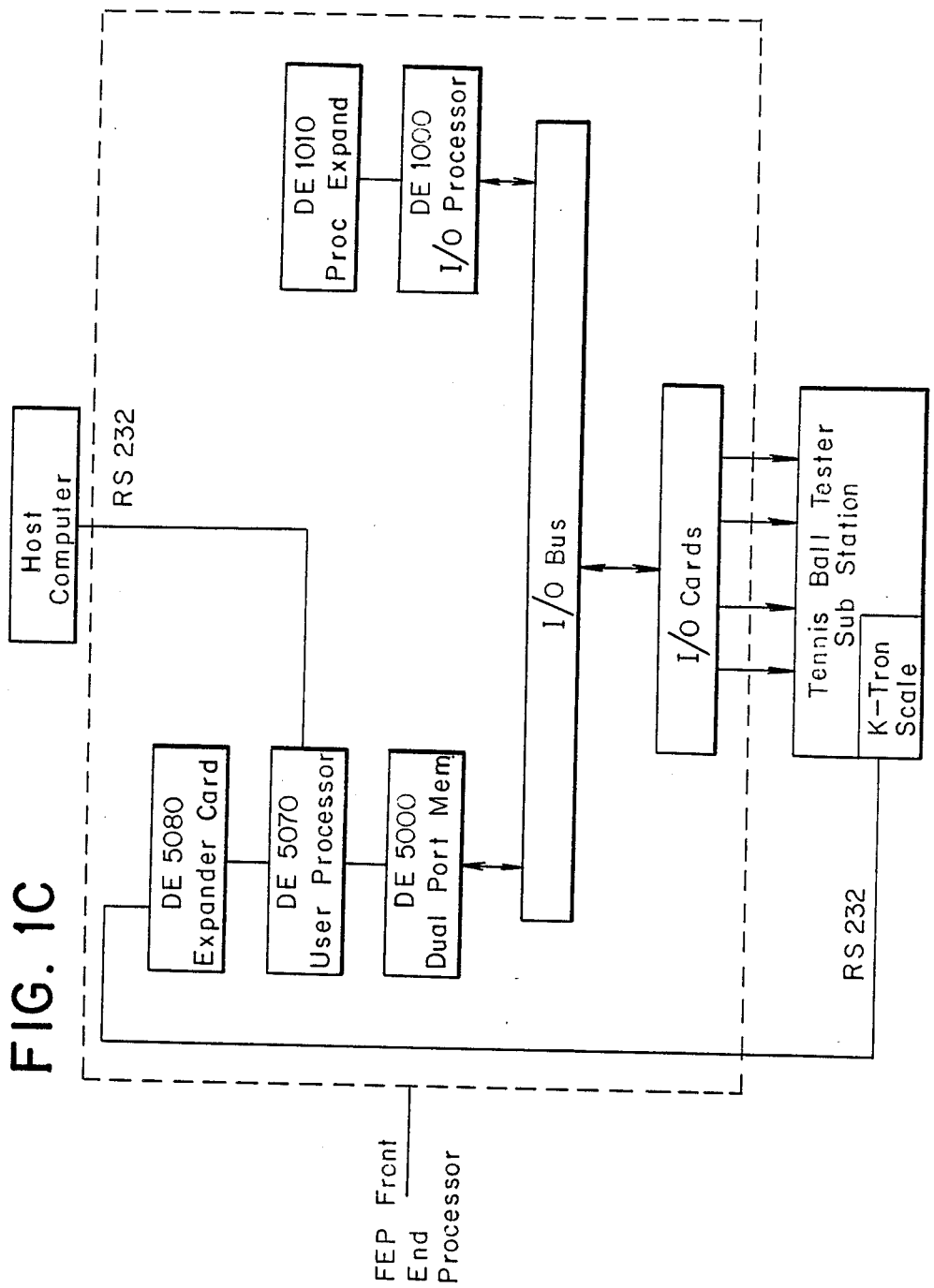
FIG. 1C is a further block diagram relating to the host computer and associated equipment.

Referring to Fig. IB, the system test equipment (Test Equip.) is operated and controlled by a central computer unit (CPU). The computer processor preferably has 68000/8MHZ/32 bit registers and a memory of 384KB RAM/250NS access time and up to 128KB ROM. An IBM 9001 Instrument Computer has been found satisfactory. Other components include real time control system (RTC); operating system (O/S) and software system (S/W). Also shown are video display console (CRT) and input keyboard (KB). Computer programs useful in operating the computer used in the system as written in as language are present in the file only, as Appendices 1-and not printed here. FIG. 1C represents the as-built system configurations.

Tennis balls used in tournaments or other official plays must meet specified standards. For example, the United States Tennis Association has promulgated the following standards for tennis balls:

The ball shall be more than two and a half inches (6.35cm.) and less than two and five-eights inches (6.67cm.).) in diameter, and more than two ounces (56.7 grams) and less than two and one-sixteenth ounces (58.5 grams) in weight.

The ball shall have a bound of more than 53 inches (135cm.) and less than 58 inches (147cm.) when dropped 100 inches (254cm.) upon a concrete base.

". . . The ball shall have a forward deformation of more than 0.220 of an inch (0.56cm) and less than 0.290 of an inch (0.74cm.) and a return deformation of more than 0.350 of an inch (0.89cm.) and less than 0.425 of an inch (1.08cm.) at 18 lb. (8.165kg.) load. The two deformation figures shall be the averages of three individual readings along three axes of the ball and no two individual readings shall differ by more than 0.030 of an inch (0.08cm.) in each case."Regulations are also specified by the Association as to the temperature, humidity and other conditions under which tests are to be performed including initial flexing of the ball before testing (precompression steps).

Figure 2:
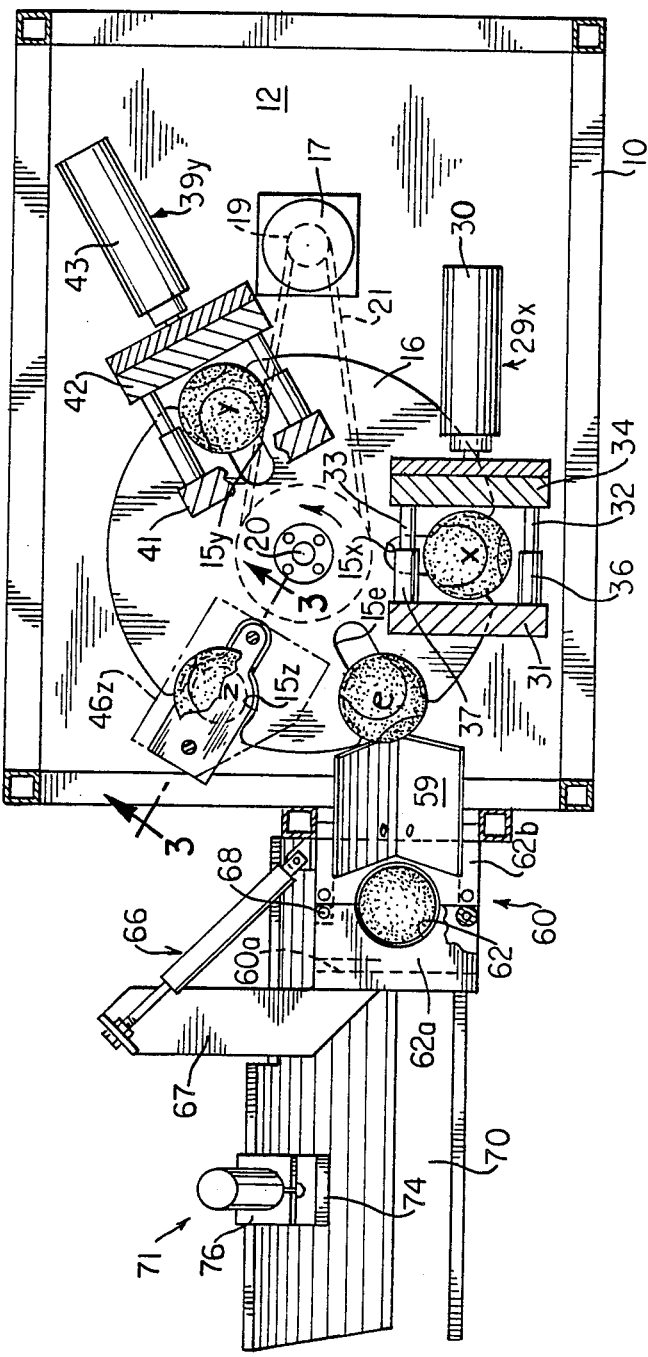
FIG. 2 is a sectional view taken along line 2—2 of FIG. 1.
Figure 3:
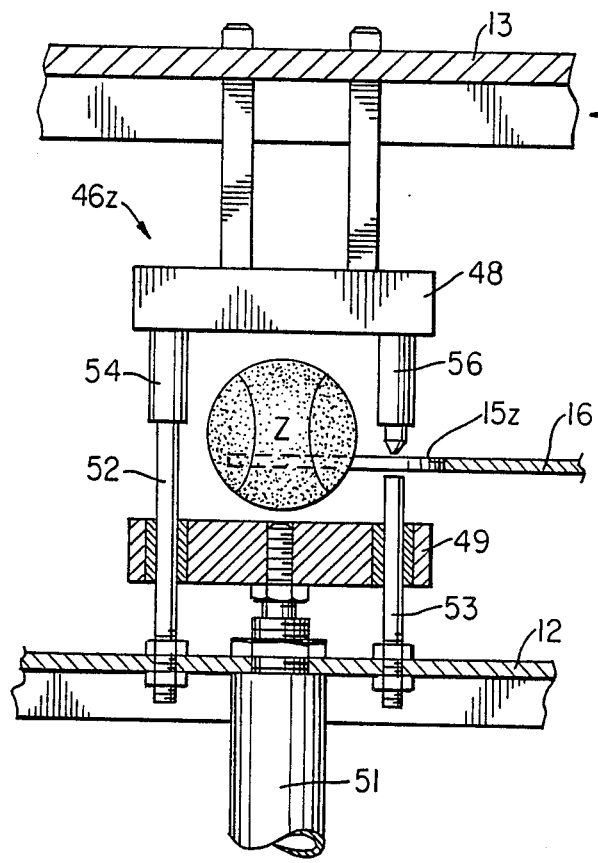
FIG. 3 is a sectional view taken along line 3—3 of FIG. 2.

With respect to FIG. 1, 2, and 3, the preconditioning station 9 functions to flex tennis balls prior to sizing, weighing and other testing. Station 9 includes frame structure 10, base 11, floor 12, and top 13. Mounted on station floor 12 is tennis ball turntable 16 having four (4) keyhole ball support wells 15x, 15y, 15z and 15e. Turntable 16 is rotated n a counterclockwise indexing manner by stepping drive motor 17, motor drive shaft 18, shaft pulley 19, table pulley-shaft unit 20 and belt 21. There are four (4) substation positions in station 9 marked x, y, z and e (FIG. 2).

The tennis balls at positions x and y are raised and lowered by pneumatic cylinder ball jacks 22, 23 positioned below balls positioned at positions x and y. Ball jacks 22, 23 serving substations x and y (substation z does not require a jack sinoe the ball is compressed in-place) include dished ball cradles 24 mounted on reciprocating pistons 26 driven upwardly by air pressure and returned by gravity. Ball cradles 24 are shaped and sized to fit through keyhole support wells 15x and 15y.

Each tennis ball to be tested is placed manually at substation x oriented to avoid compression of a seam. Ball 1 (the first ball in a series of balls to be tested) is positioned at substation x and the precompression process is started up through operation of the computer control equipment, jack 22 lifts the Ball 1 up to the position shown in dashed lines 28 (FIG. 1). While in this position Ball 1 is compressed by horizontal ball compressor unit 29x which includes stationary jaw plate 31, a pair of spaced-apart guide rod-sleeves 32, 33, movable jaw plate 34, and pneumatic cylinder 30. Movable jaw plate 34 is driven toward stationary plate 31 causing compression of Ball 1 until it engages sleeves 36, 37 of guide-rod sleeves 32, 33 respectively. Sleeves 36, 37 serve to limit the amount of ball compression. Movable jaw plate 34 is retracted; jack 22 lowered, and Ball 1 returned to well 15x. Turntable 16 then rotates counterclockwise (FIG. 2) until Ball 1 reaches substation 115y where jack 23 elevates Ball 1 for compression by ball compressor unit 39y. Compressor 39y, like compressor 29x, has fixed jaw 41, movable jaw 42 and pneumatic drive cylinder 43 (FIG. 2). Compression of Ball 1 at substation y is accomplished along an axis of the ball different from the axis of compression at substation x.

Upon the subsequent counterclockwise movement (indexing) of turntable 16 to substation z, Ball 1 is further compressed by compressor unit 46z mounted betweem floor 12 and top 13 for vertical movement. Movable horizontal jaw 49 is moved toward fixed jaw 48 by cylinder 51. Movable jaw guides 52, 53 and stop sleeves 54, 56 are shown. Guide 56 is interrupted to avoid interference with turntable 16 (FIG. 3).

Subsequent indexing of turntable 16 may move Ball 1 through one or more cycles of substations x, y and z for further treatment or Ball 1 may be directed to exit position 15e where discharge jack 57 including inclined head 58 is raised to cause Ball 1 to roll into exit chute 59 for delivery to the size gauge station 61 (see FIGS. 1 and 2). Size gauge station 61 includes three (3) superimposed circular openings (oversize upper opening 62, undersize middle opening 63, and small ball rest opening 64) formed by superimposed half portions 62a, 62b, 63b and 64a, 64b in a frame box section 60, one section 60a stationary and one section 60b pivotal to expand the circular openings to release the ball upon completion of the gauging of its size.

Ball 1 reaches uppermost opening 62 as it is discharged from precompression exit chute 59. If Ball 1 is oversized, it will not pass through uppermost circular opening 62. If Ball 1 has a diameter within the desired range, it will not pass openings 63 and come to rest there (see FIG. 1). If the Ball is too small, it will pass both upper and middle openings 62, 63 and come to rest on lower opening 64.

Figure 4:
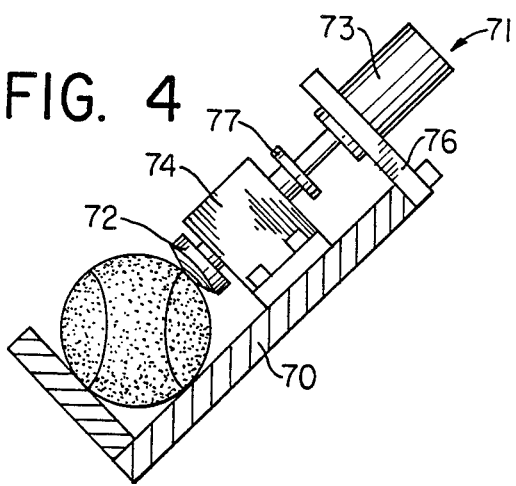
FIG. 4 is a sectional view taken along line 4—4 of FIG.

Upon the next indexing of the test system, size gauge box 60 is opened a small distance by operation of pneumatic piston arrangement 66 including pivot arm 67 for pivotally moving box section 60a about axis 68 causing Ball 1 to drop onto inclined size-measuring trough 70. Ball 1 rolls down trough 70 until it engages side mounted measuring unit 71 which includes measuring head 72 (FIG. 4). Head 72 is mounted on reciprocal piston 73 supported in bearings 74, 76 and normally urged by gravity and a spring (not shown) downwardly until ring stop 77 engages bearing mount 74. When rolling Ball 1 engages angular head 72, it forces head 72 upwardly to allow the Ball 1 to clear head 72 without stopping (though slowing) the movement of Ball 1 along the trough. The highest position of the piston 73 is measured by a sensor (not shown) as Ball 1 passes. This measurement is used by the computer to determine the diameter of Ball 1.

Figure 5:
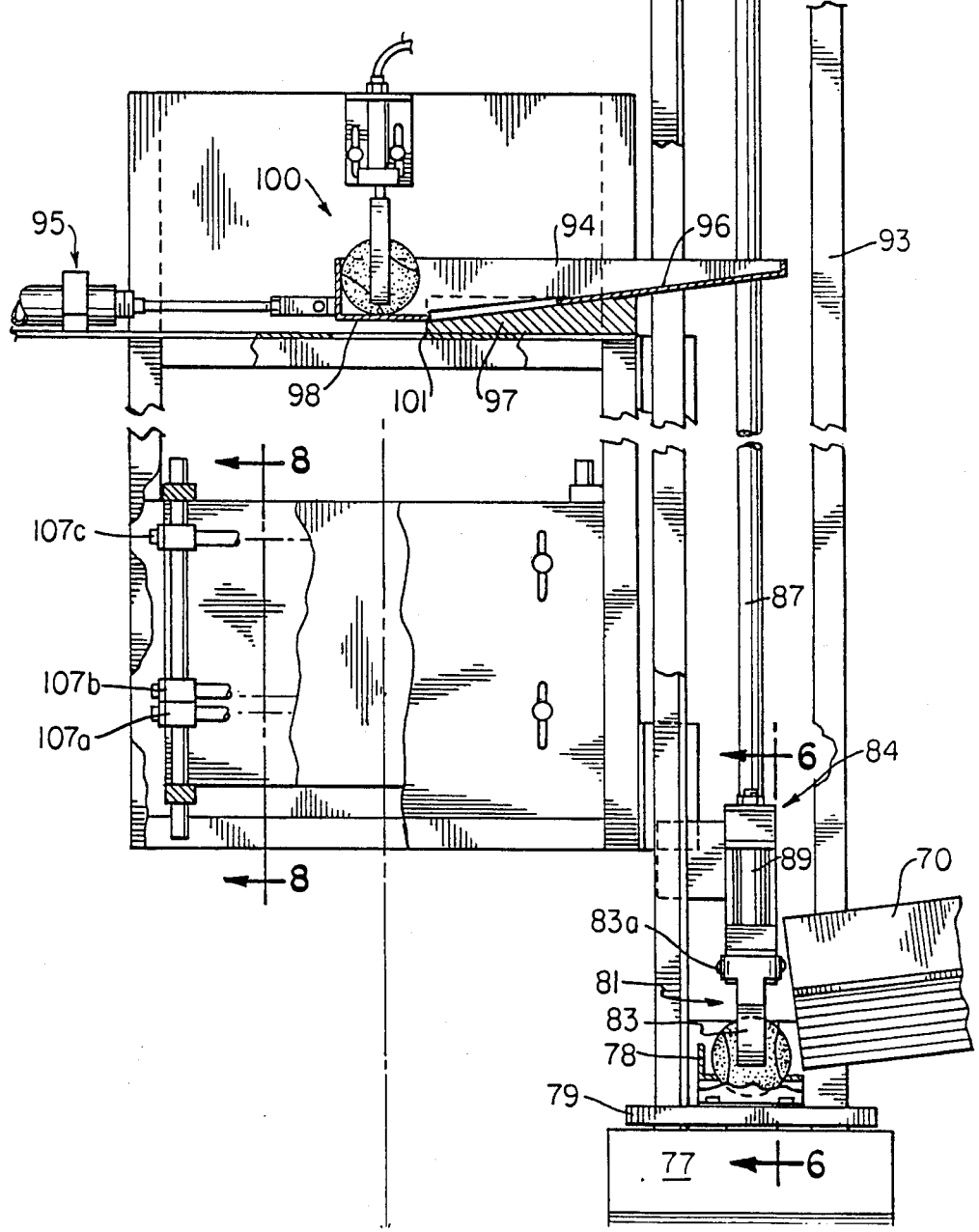
FIG. 5 is a front elevational view of the bounce test station.
Figure 6:
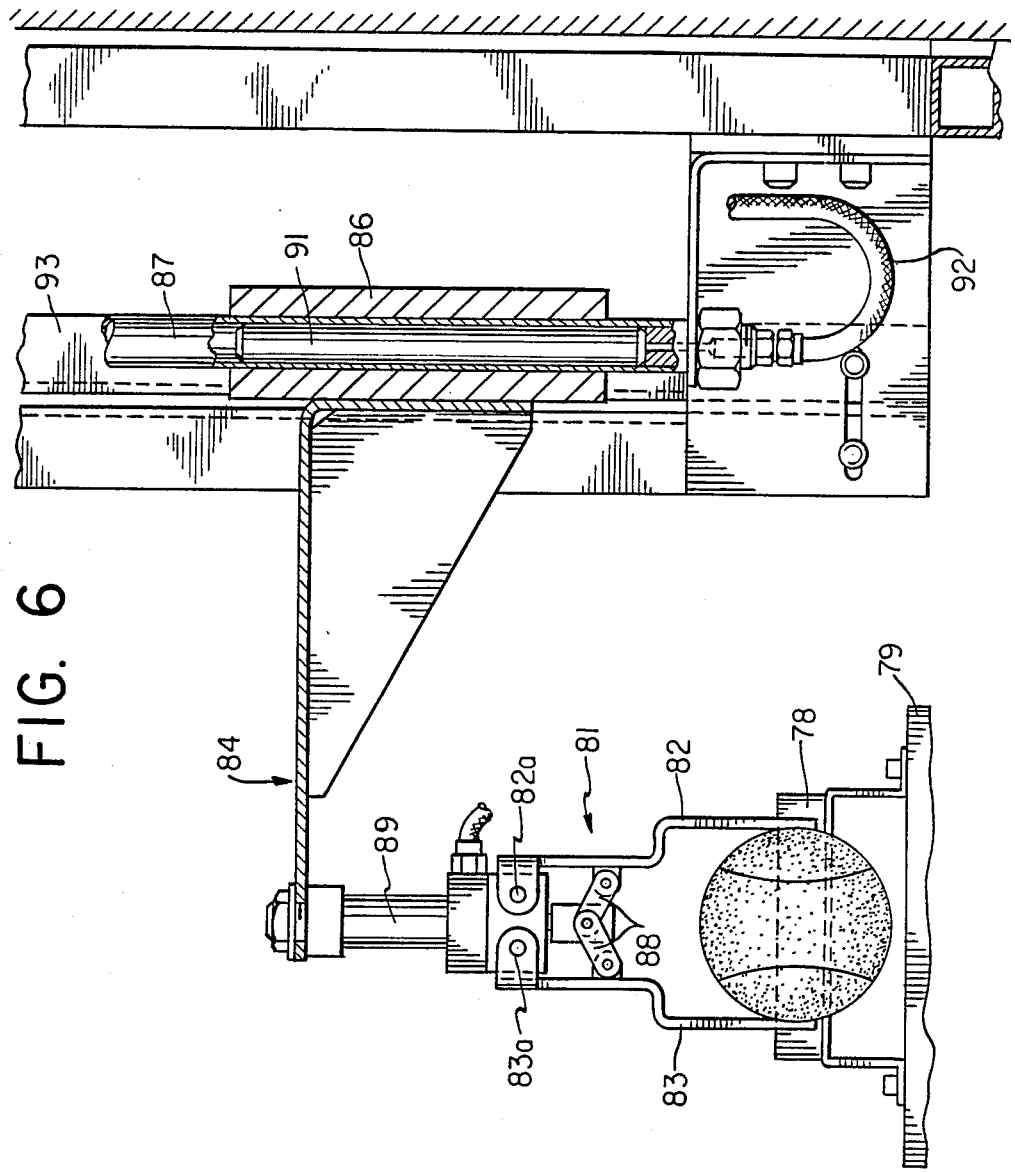
FIG. 6 is a sectional view taken along line 6—6 of FIG. 5.

Turning now to FIGS. 5 and 6, Ball 1 exits trough 70 onto weigh scale 77. Scale 77 includes ball seat 78 connected to movable scale plate 79 which moves downwardly in response to the weight of Ball 1. Any commercial weigh scale capable of weighing a tennis ball may be used. In the next sequential advance of the testing system Ball 1 is readied for a bounce test as it is seized by air-operated gripper unit 81 which has two fingers 82, 83 pivotal about pins 82a, 83a respectively. Pins 82a, 83a are mounted on cylinder and lifting frame 84. Lifting frame 84 includes metallic sleeve 86 mounted on vertical tube track 87. Fingers 82, 83 are opened and closed by arms 88 attached to air reciprocating piston 89 (FIG. 6). Cylindrical ball lifting frame 84 is caused to move up and down along tube track 87 by the movement of a cylinder magnet 91 slidably positioned inside the tube track 87 which magnet 91 emits sufficient magnetic forces to cause metallic sleeve 86 (together with its lifting frame 84) to follow magnet 91 up and down tube track 87. Movement of magnet 91 is accomplished by air pressure in the tube track 87 supplied through air hose 92. Also shown is bounce test station frame 93.

As Ball 1 is elevated ball catcher pan 94 moves, as directed by the central computer, from the position shown in FIG. 5 to the left by cylinder-piston unit 95 to permit lifter frame 84 to pass. Upon reaching a height above the catcher pan 94, catcher pan 94 moves right to the position of FIG. 5 to catch Ball 1 as released by the gripper unit 81. Ball 1 then rolls down pan ramp 96 onto inclined pan mount piece 97 and finally to horizontal pan rest section 98 where second gripper unit 100 engages and holds Ball 1. Second gripper unit 100 has the same construction and operation as gripper unit 81. Ball 1 is ready for the bounce test upon the subsequent indexing of the system at which time, pan 94 is moved right to place pan drop hole 101 under Ball 1. Second gripper unit 100 then releases Ball 1 which starts its descent.

Figure 7:
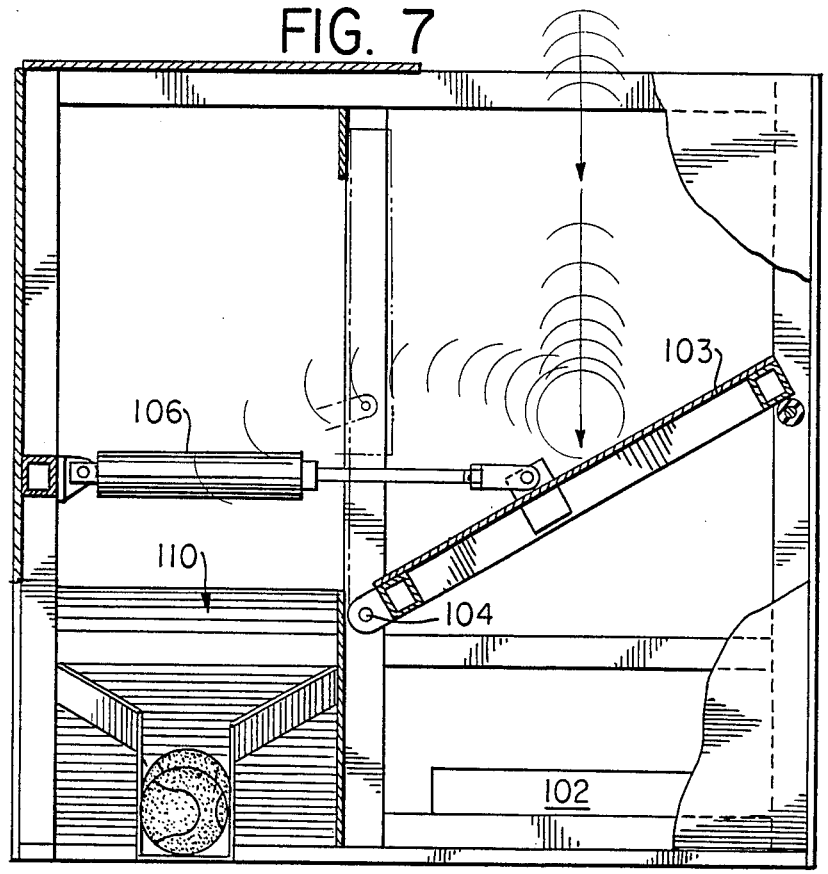
FIG. 7 is an enlarged partial front elevational view of the bounce test station.
Figure 8:
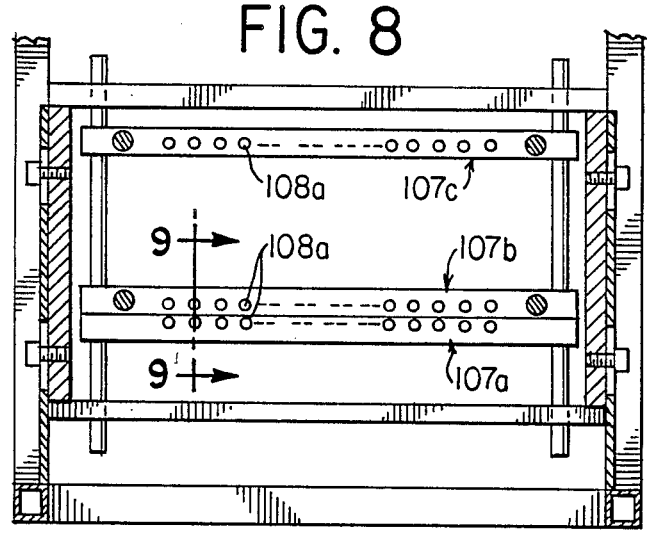
FIG. 8 is a sectional view taken along line 8—8 of FIG. 5.

Ball 1 falls a selected distance until it strikes stationary bounce plate 102 and rebounds upwardly (See FIG. 7). Prior to Ball 1 reaching the deflection door area during its descent, door 103 is pivoted about axis 104 to its open position by air cylinder unit 106. As Ball 1 rebounds upwardly it passes through one or more infra red detector beam arrays 107a, b, and c providing data as to both height of rebound and angle of rebound of Ball 1. Each array has a plurality of infra red beam units 108 with each unit having a transmitter 108a and a receiver 108b (FIG. 9) spaced apart a sufficient distance to permit passage of the descending and rebounding balls. The breaking of the infra beam of one or more beam units 108 indicates the presence of Ball 1. Lowest array 1107 a is placed at the minimum height to which the ball is required to bounce to meet the desired standards. If the Ball 1 does not pass through one or more beam units 108 or lower array 107a, the minimum bounce has not been attained. Middle array 107b is positioned close to the lower array 107a and upper array 107c is positioned at the maximum bounce level.

Since a dozen or more beam units 108 are used in each array, the passing of Ball 1 through certain beam (or beams) provides information from which can be calculated the angle of bounce, height and total distance of the bounce. Alternatively, array unit 107b may be turned ninety (90°) degrees so that its beam transmissions are perpendicular to the beam transmission of its unit 107a.

As the ball descends from it rebound, deflector door 103 is closed to deflect Ball 1 into collection hopper 110. Ball 1 is manually removed from the collection hopper 110 and thereafter manually placed in the compression station as hereinafter described.

In the preferred mode of operation, the preconditioning routine (in which Ball 1 is compressed three times in each substation x, y and z) is followed for a total of nine (9) compressions. It will be seen that Ball 1 is subjected to eighteen (18) separate operations including conditioning, measuring, testing and transporting (see the chart of Fig. 12). Ball 2 is manually placed at substation x following the first indexing of the system after Ball 1 has been compressed at substation x and advanced to substation y. Subsequent balls 3, 4, 5, etc. are similarly manually placed at substation x. All balls follow the same operation in the same sequence as Ball 1 with all balls arriving in collection hopper 110.

Figure 10:
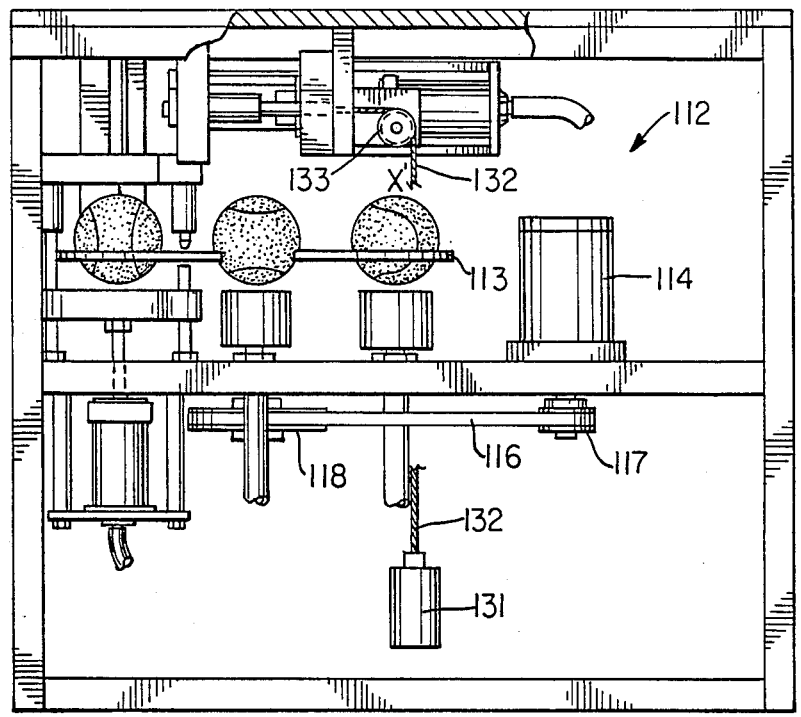
FIG. 10 is a front elevational view of the compression station.
Figure 11:
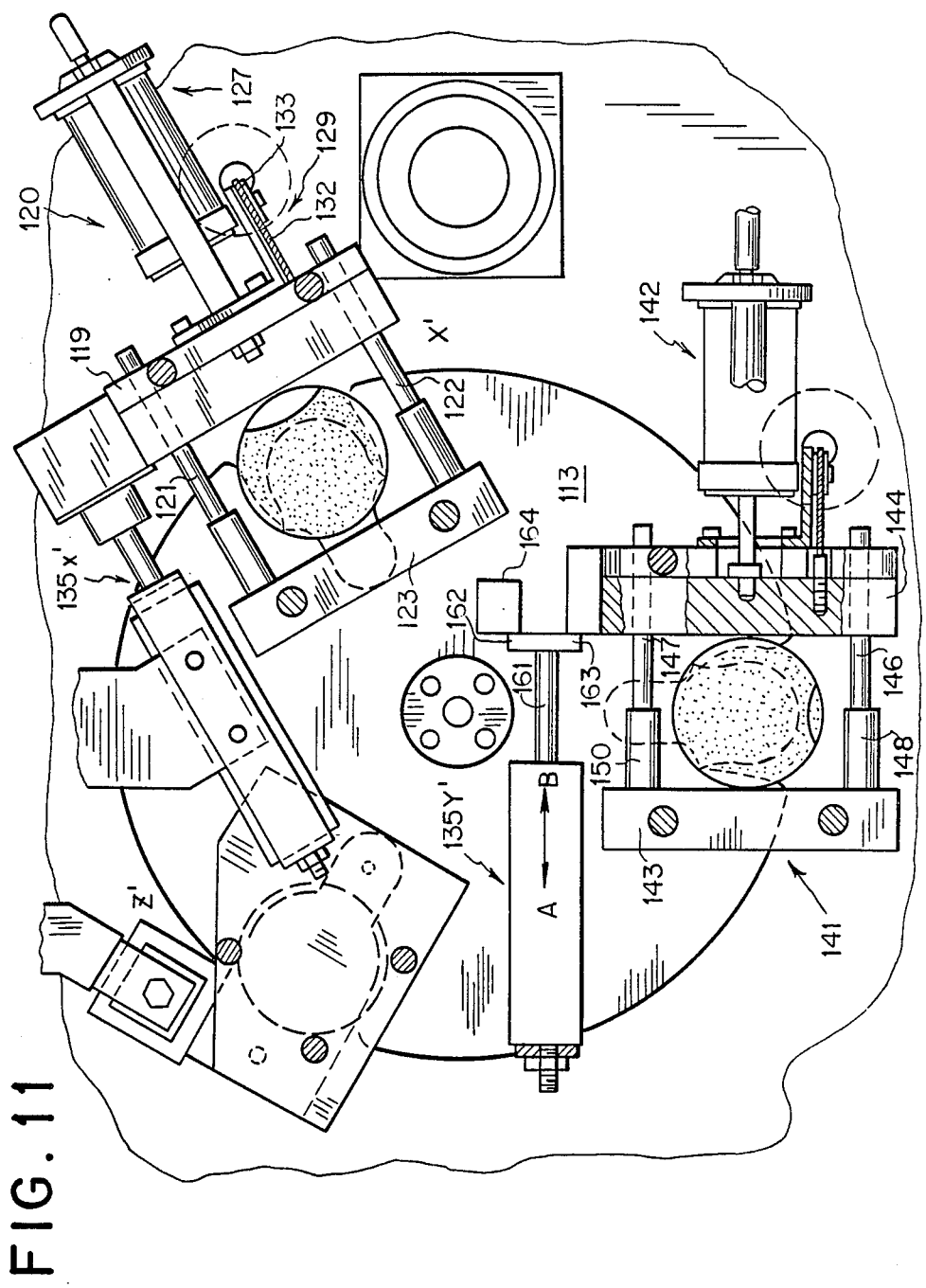
FIG. 11 is a plan view of the compression station.

Turning now to FIGS. 10 and 11, the final testing station is described. Ball 1 (and other balls) is removed from collection hopper 110 and placed in ball compression unit 112 for testing. Compression unit 112 includes turntable 113 driven by motor 114 through belt 116 and pulleys 117, 118. Ball 1 is placed in substation x' for deformation.

Movable platen 119 of deformer unit 120 translates on guide rods 121, 122 mounted in fixed platen 123. Sleeves 124, 126 function as stops limiting travel of the movable platen 119 by air drive unit 127. Movable platen 119 is urged away from Ball 1 by counterweight unit 129 comprising weight 131, wire 132, and pulley 133. Counterweight unit 129 places a predetermined pull on movable platen 119 with air piston unit 120 urging platen 119 in the opposite direction.

Figure 11A:
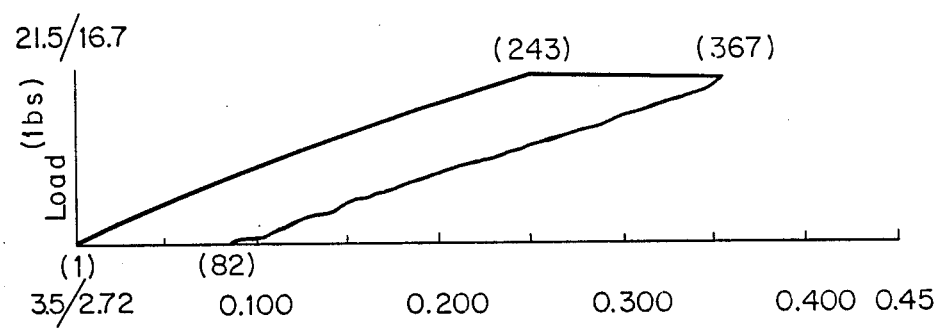
FIGS. 11A and 11B depict, in graphical form, forward and reverse ball deflection curves.
Figure 11B:
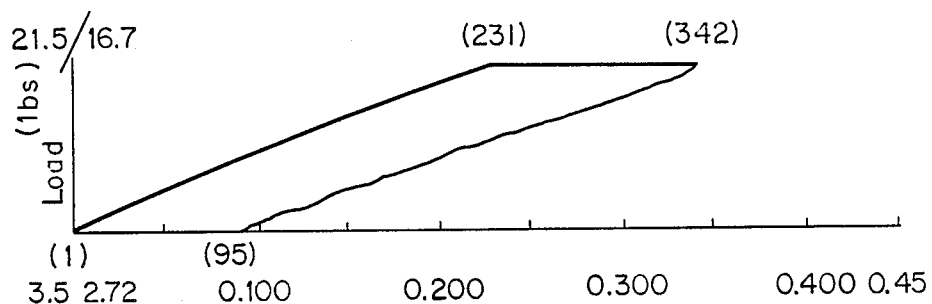

The air cylinder unit 120 applies an initial contact force of 3.5 lbs. against Ball 1. At time $T_1$, a zero displacement reading is stored in the computer's memory. At Time T1, the force on Ball 1 is increased to 21.5 lbs. (See FIG/ 11A). At Time T1 plus five (5) seconds, the forward deformation of the Ball 1 (0.243 inches: FIG. 11A) is measured by displacement transducer 135x', which measurement is stored in the computers memory, and displayed on the CRT (FIG. 1B ). At Time T2, (milliseconds after T1+5), pressure is applied deforming Ball 1 to 1 inch. Upon reaching the 1 inch deformation, the pressure is relieved, and the force on Ball 1 restored to 21.5 lbs. (3.5+18) at time T3. At time T3 plus 10 seconds, the reverse deformation reading is stored in memory, displayed on the front panel, and a green indicator lamp (not shown) turns on if Ball 1 passes both deformation specification, (or a red lamp) if Ball 1 fails. Ball 2 is subjected to a similar test sequence with differing deflection results (Fig. 11B).

Figure 13A:
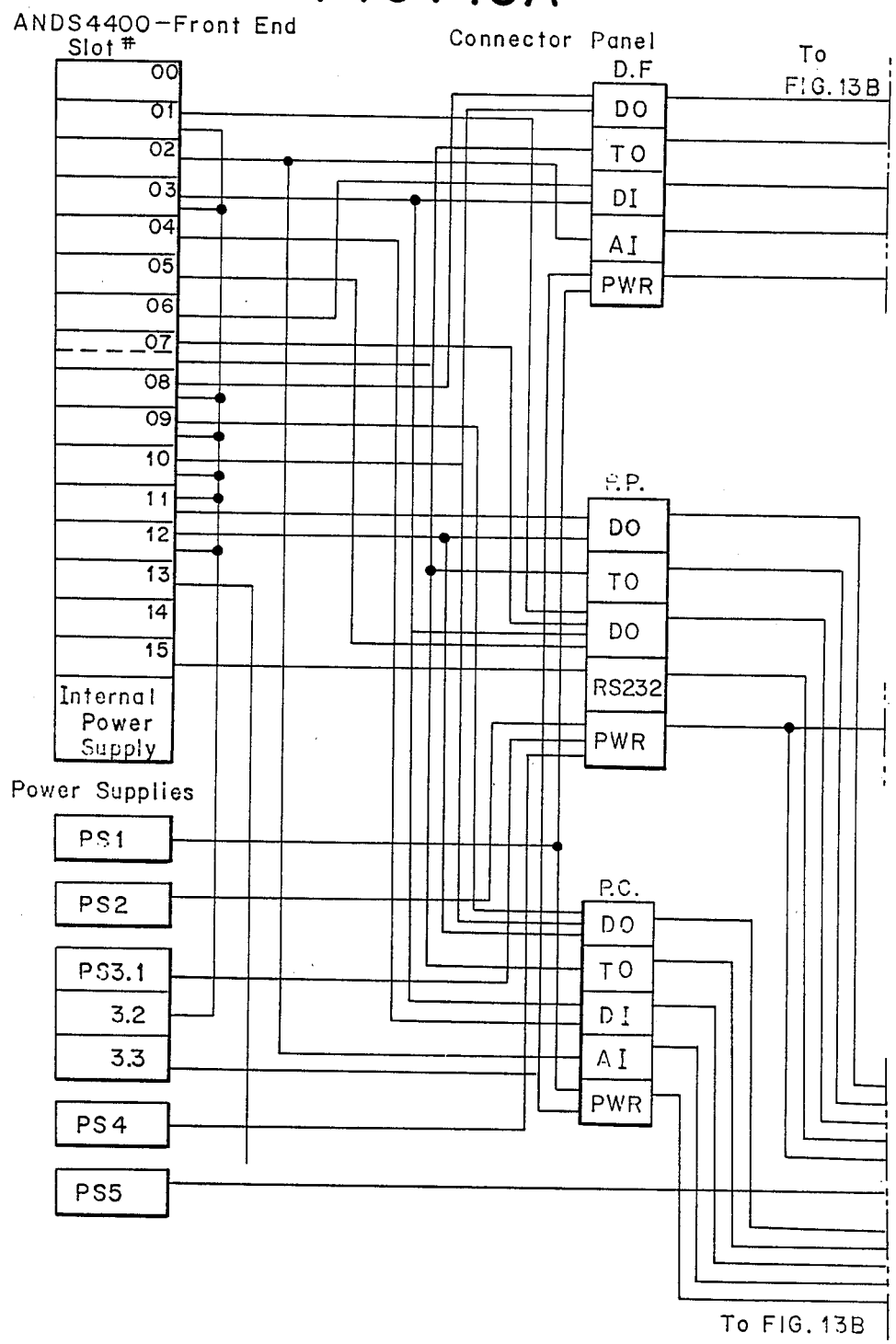
FIGS. 13A—13 D show the wiring diagram.
Figure 13B:
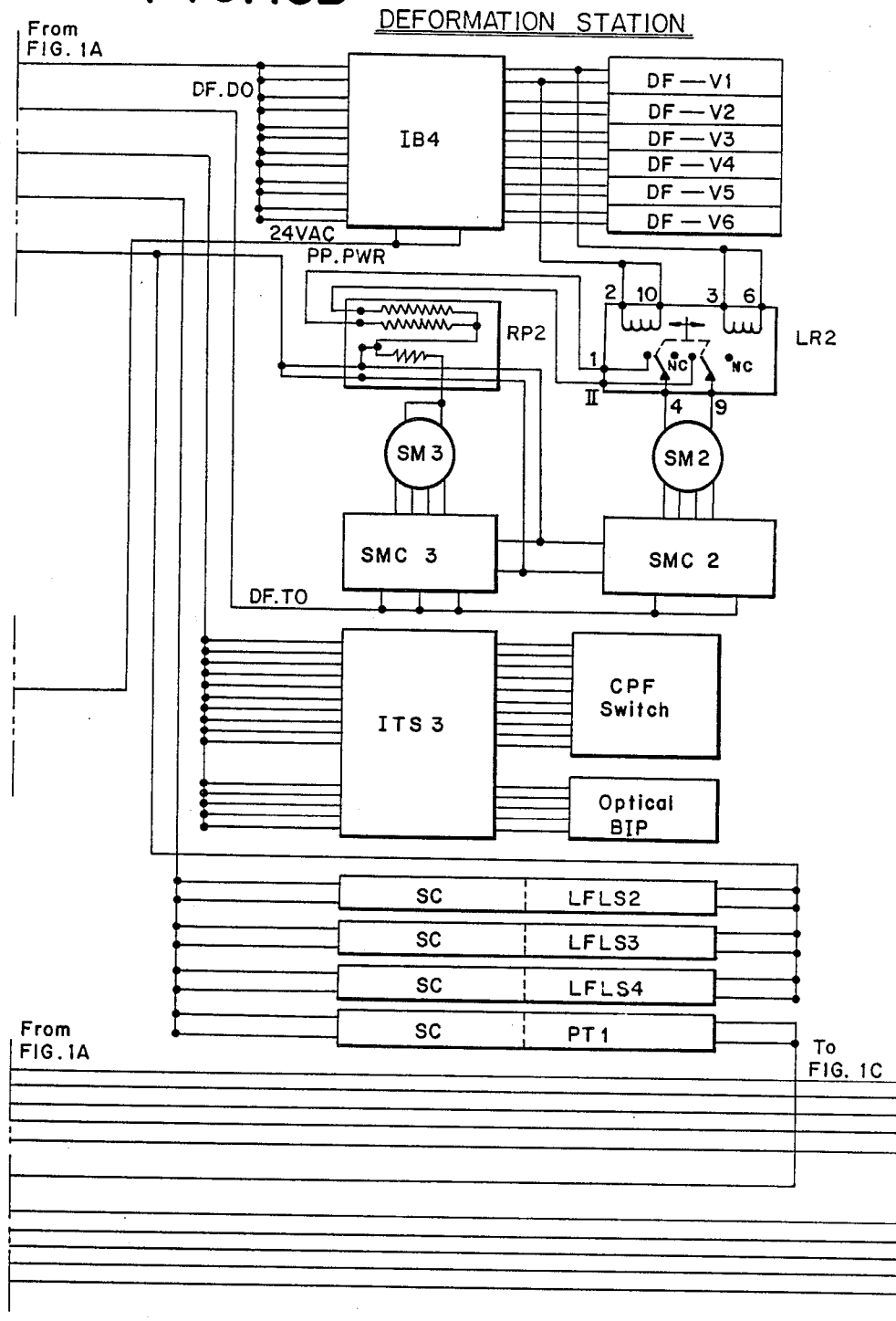

Upon completion of deformation Ball 1 at substation xx', the turntable 113 is indexed clockwise (as shown in FIG. 11) to transport Ball 1 to substation y, for further compression testing along a different axis of Ball 1. Ball compression unit 141 includes the same components as ball compression unit 120 including pneumatic drive assembly 142, fixed and movable ball platens 143, 144; platen guides 146, 147 and sleeves 148, 150. Transducer 135y includes cylinder 160, cylinder piston 161 and left and right magnetized piston feet 162, 163. Metal frame mounted stop 164 and metal movable platen 144 engage and disengage feet 162, 163 to limit the travel of piston 161. When piston 161 is moved in the arrow A direction foot 162 remains engaged to move platen 144 through the force of magnetism. When piston 161 moves in the arrow B direction, foot 162 engages stop 164 where it is held through the force of magnetism until platen 144 returns to pick up and move piston 161 in a return stroke. This arrangement permits the travel of transducer piston 161 to be limited to increase accuracy of its measurements. From compression unit 141, Ball 1 is then carried by turntable 113 to substation z' for compression along a different axis. Ball compression unit 151 is constructed similarly to units 120, 142. Compression unit 151 is mounted with compression platens positioned for operation toward and away from each other in a vertical plane. Displacement transducer 135y' measures the location of the movable platen which location is fed to the computer. t In FIGS 13A-D, electrical power and control circuits and components of the system are shown. Turning first to FIG. 13D, preconditioning subsystems PC-V1 through PC-V6 are powered from power supplies PS-1-5 (see FIG. 13A) through relay interface board (IBI). Preconditioning subsystems PC-V1 through PC-V6 include operation of three (3) preconditioning substations x, y, and z, discharge station e, go-no-go size gauge and diameter size gauge. Stepping motor controller (SMC1) controls stepping motor (SM1) which causes precondition station turntable 16 to index by turning a selected number of degrees and then stopping for a preset time before commencing the next indexing operation.

Cylinder positioning switches (CPl) actuate jacks 22, 23 to raise each ball at substations x and y for preconditioning and thereafter lower each ball for further turntable transport. Optical ball-in-place (BIP) units indicate when the ball is properly located.

Figure 13C:
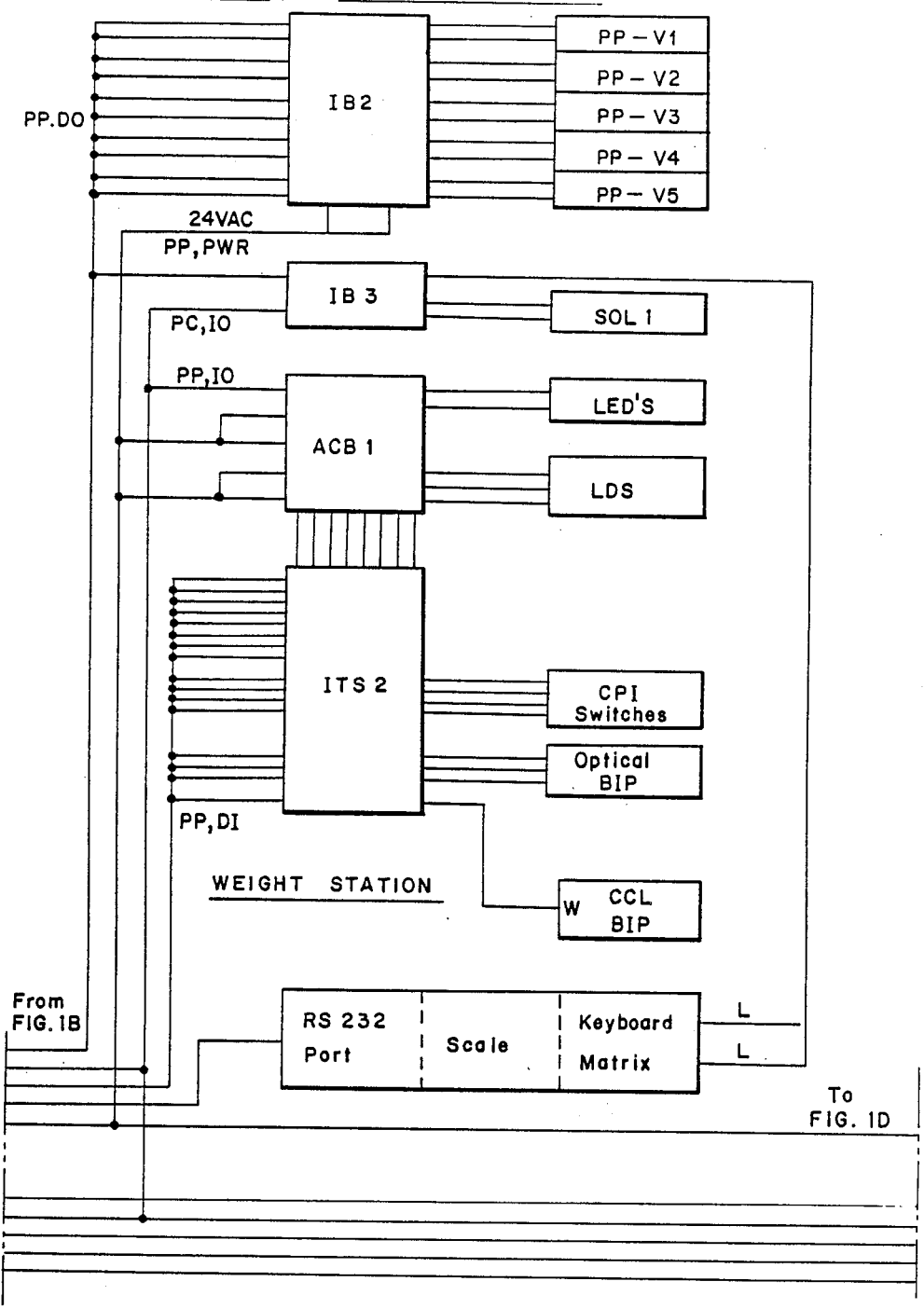
Figure 13D:
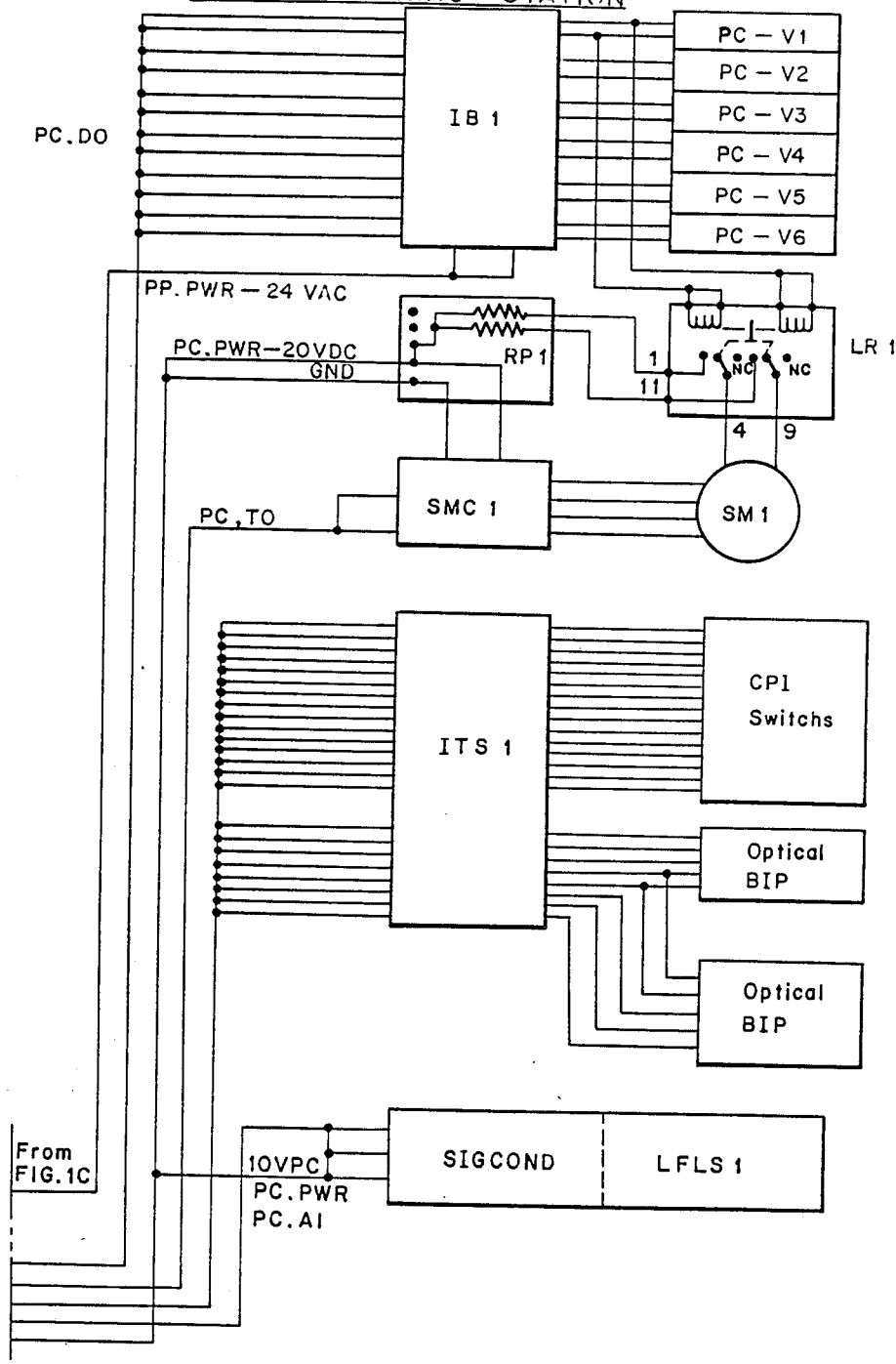

Turning to FIG. 13C, pick and place units (ball gripper units) (PP-Vl through PPV-5) are powered through relay interface board (IB2). Units (PPV1 through PPV-5) operate solenoid valves of gripper ball units which lift, hold, and drop the balls. Solenoid valves also operate the ball pan collector and the ball deflector door. Also shown is relay interface board (IB3) which distributes power to keyboard, scale and communicates cable (RS232). Further shown is input terminal strip (ITS2) which is connected to cylinder control switch (CPl) and ball-in-place switch (BIP).

With respect to FIG. 13B, relay interface board (IB4) serves subsystems (DF-V1 through DF-V6) with stepping motors (SM2,3) controlled by stepping motor controller (SMC2,3) respectively. Also shown are low friction linear sensors (LFLS2-4) and pressure transducer (PT1).

Fig. l3A shows connector panels, the preconditioning subsystem (PC), pick-and-place subsystem (PC) and deformation subsystem (DF). Power supplier units are also shown (PS1, 2, 3.1, 3.2, 3.3, 4 and 5).

Figure 14A:
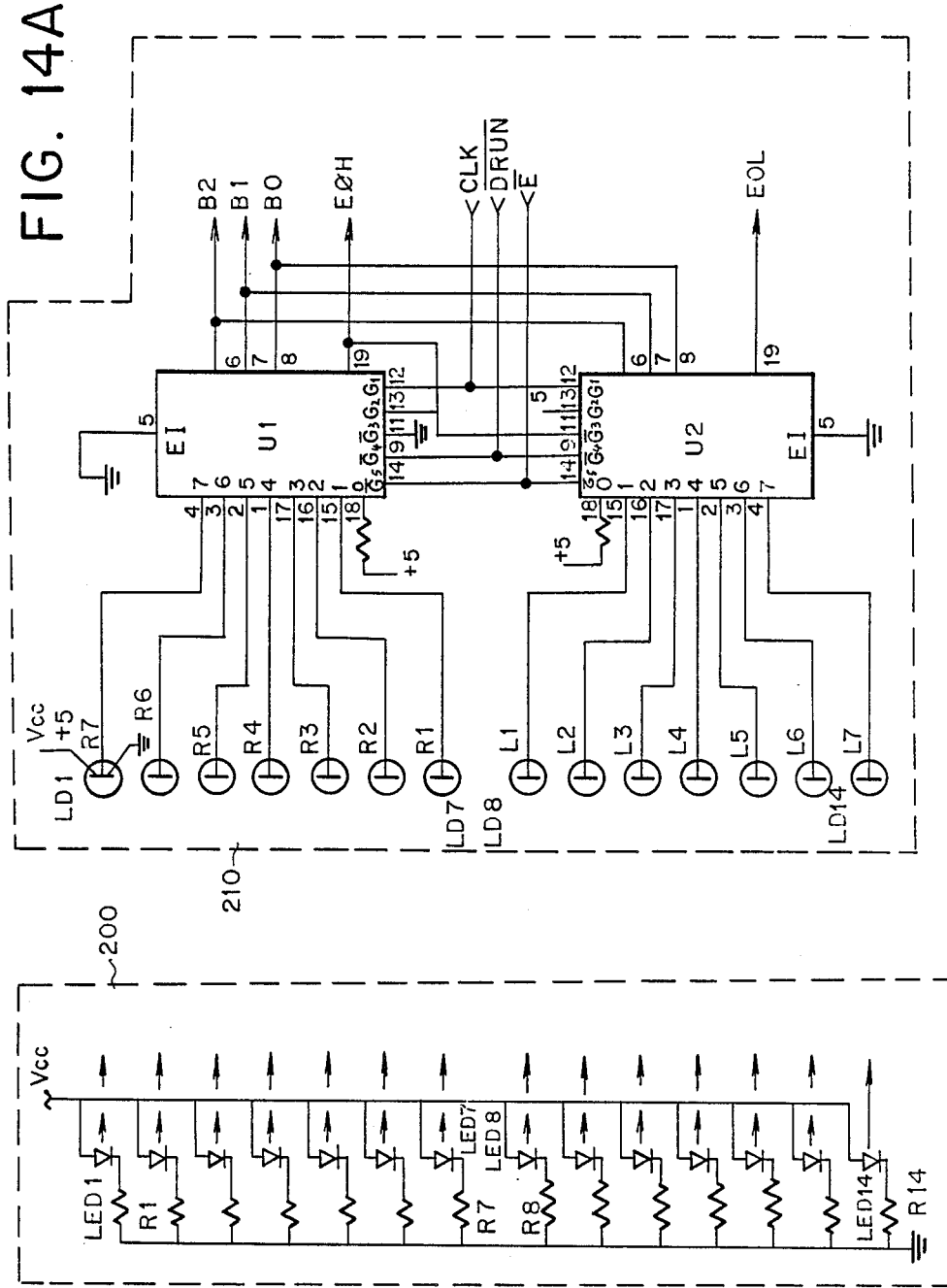
FIGS. 14A–14C show logic control circuitry related to the bounce test station operation.

Finally, referring to FIG 14A, there is shown an infra red detector beam array comprising optical aray LED board 200 which produces 14 essentially parallel light beams and optical array detector and encoder board 210 which detects the presence of said light beams.

Optical array LED board 200 comprises light emitting diodes (LEDs) LEDI through LED14, which are arranged in a linear fashion. Associated with each LED is a series resistor to ground (R1-R14) serving to limit current through the LEDs. Resistors R1 through R14 illustratively are 18 ohm, 1 watt resistors while LEDs LED1 through LED14 illustratively are infrared emitting diodes of the type G.E. F5D1.

Optical array detector and encoder board 210 comprises light detectors LD1 through LD14 arranged in a linear fashion such that each light detector may detect any interruption of the light beam produced by its LED counterpart on optical array LED board 200. LD1 through LD7 comprise the seven right side light detectors while LD8 through LD14 comprise the seven left side light detectors. LD1 through LD7 are input to U1, a 74LSOO quad 2 Input NAND Gate chip while LD8 through LD14 are input to U2, a 74LSII Tri 3 Input AND Gate chip. U1 and U2 produce a 3 bit address on lines B$\emptyset$, B1 and B2 indicating which infra red beams have been interrupted. This 3 bit address indicates which beams from the center of the array have been interrupted. To determine whether the interrupted beam is on the right or left side,, lines EOH (right side) and EOL (left side) are used.

Figure 14B:
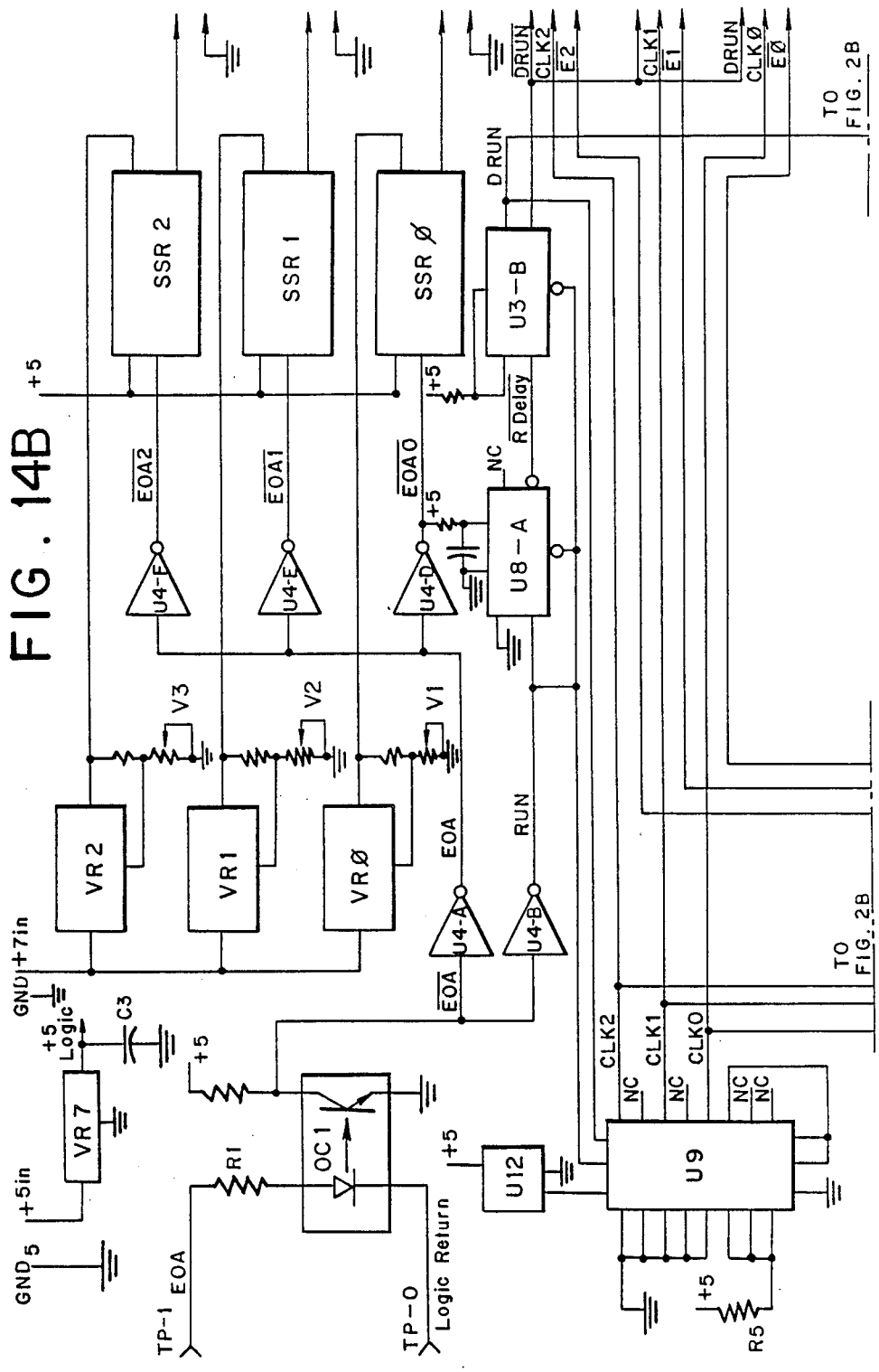
Figure 14C:
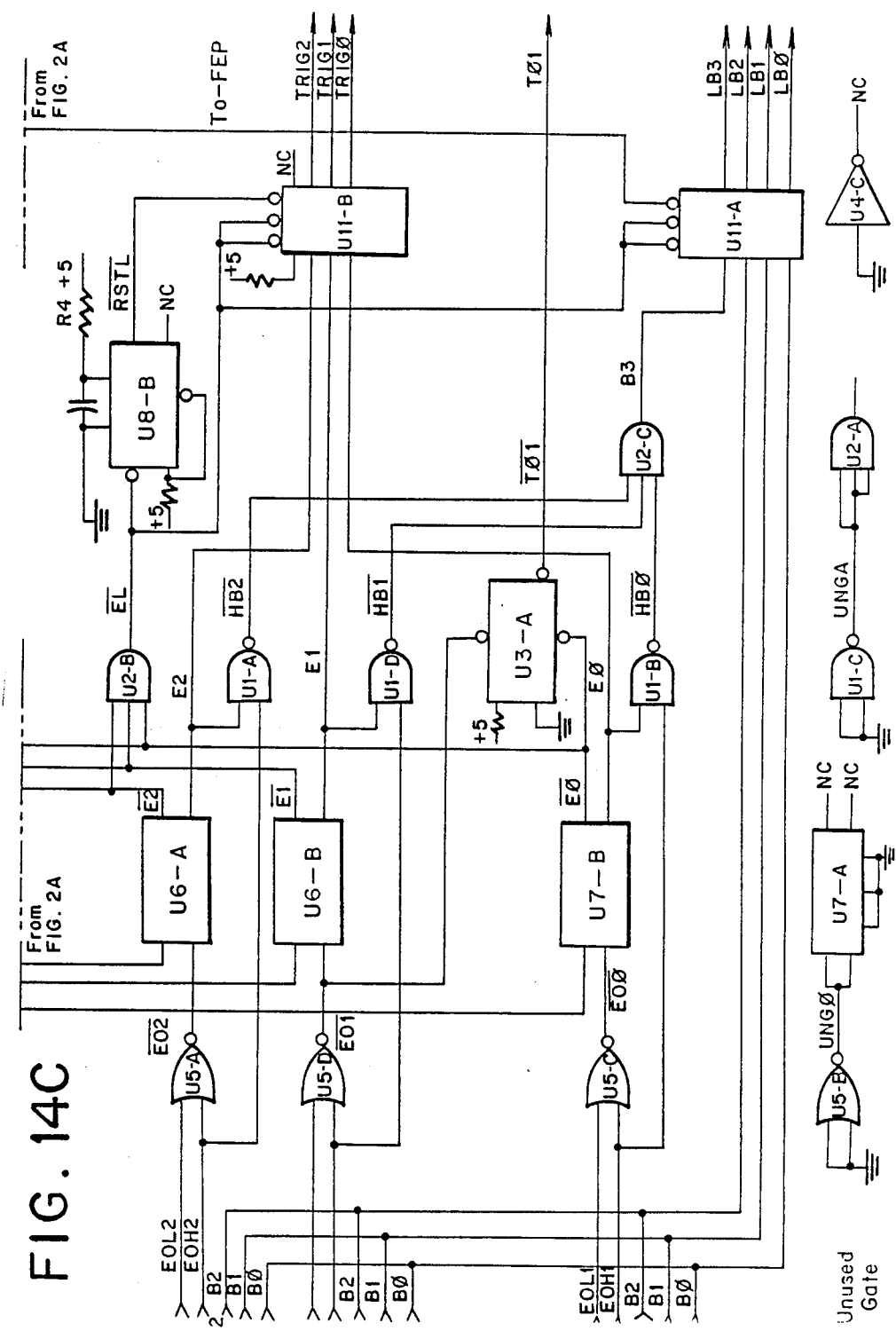

Turning to FIGS. 14B and 14C, the optical timing and output circuitry for the bounce test is shown. In practice, each of the optical arrays, one of which is depicted in FIG. . 14A, is enabled and disabled under computer control. Enabling of an array exists during a window or slice in time.

Clock generator U12 of FIG. 14C generates a 4MHz clock signal which is input to -8 bit shift register U9 of FIG. 14B. U9, illustratively a 74199 device, is computer controlled and produces enabling signals on lines CLK$\emptyset$, CLK1 and CLK2 functioning as three windows for the three LED arrays. CLK$\emptyset$, CLK1 and CLK2 are input to U7B, U6B and U6A of FIG. 14C respectively. U6 and U7 are 74120 type Dual Pulse Synchronizers/Drivers. Signals EOL and EOH which are used to determine whether an interruption exists on the left or right side of an array are input to U6 and U7.

More specifically, signals EOL2, EOH2 which indicate whether an interruption exists for the left or right side of the uppermost array are input to NOR gate U5-A. Similarly, signals EOL1, EOH1 corresponding to the center array are input to NOR gate U5-C and signals EOL$\emptyset$, EOH$\emptyset$ corresponding to the lowest array are input to NOR gate U5-D. Nor gates U5-A, U5-D and U5-C are input to drivers U6-A, U6-B and U7-B respectively. The output of these three drivers are input to U11, a 74116 type Dual Quad Latch. The three output lines of U11B are input to a front end processor FEP and indicate which of the three arrays is presently being interrupted. The three bit address on lines B$\emptyset$, B1, and B2 from each array indicating which beams have been interrupted are input to U11IA. The output of UIIA is input to the FEP over lines LB$\emptyset$-LB2 and thus represents which beams have been interrupted. The output of AND gate U2-C is input to U11A and indicates whether the interruption exists on the right or the left half of an array. U11A outputs this signal to the FEP on line LB3.

Flip Flop U3-A outputs a pulse on line T$\emptyset$1 which synchronizes the resetting of the arrays. Multivibrator U8-B of FIG. 14C serves to hold the data of U11-B for a predetermined amount of time before sending such data to the FEP.

Turning back to FIG. 14B, optocoupler OC1 serves to isolate input noise from the system as well as to provide power to the optical arrays. Signal EOA is input to OCI which outputs its complement. Inverter U4-A inverts this signal to provide inverters U4-D, U4-E, U4-F with the EOA signal. The output of these three inverters are input to 30 solid state relays SSR , SSR1, SSR2 respectively. Voltage regulators VR$\emptyset$, VR1 and VR2 are each individually adjusted by a potentiometer, thus providing a precise voltage output to relays SSR$\emptyset$, SSR1, SSR2 respectively. The outputs of these three relays are then used to power the optical arrays.

I claim:

1. A method of transporting, testing, measuring and performing other operations on a resilient object in a selected order comprising
    (a) providing a plurality of operating stations including a first operating station in which objects are flexed a plurality of times, an intermediate test operation station and a last operating station in which the objects are subjected to predetermined loads and deflections to deform the object;
    (b) providing means for transporting the object from operating station to operating station;
    (c) controlling each operating station and the transporting means using a central control system, said system in turn comprising computer means including memory means; input means for inputting signals to the computer means; and
    output means for outputting signals from the computer means to control the operating station and transport means so that an object placed in the first operating means is automatically operated on at the first operating station and thereafter automatically transported to the next operating station as determined by such output means.

2. The method of claim 1 in which the first and last operating stations are combined as one station.

3. The method of claim 1 in which the central system includes in addition a display means for displaying input signals from the input means and also includes means for printing output signals.

4. Apparatus for transporting, testing, measuring and performing other operations on a deformable object comprising
    (a) at least one operating station for subjecting the object to repeated deflections;
    (b) at least one test operating station;
    (c) transport means for transporting the object from one station to another station;
    (d) power means for operating such stations and transport means;
    (e) control means for controlling such power means; said control means including central computer means operating system means, file management means, and real time control means whereby the control means operates such operating deflection station, test station, and transport means to perform such operations on the object in a first station, transport the object to a second station and performs such operation on the object at the second station.

5. The apparatus of claim 4 in which there are a plurality of operating stations including stations for compression, weighing, sizing and dropping the object in a selected sequence.

6. Apparatus for conditioning, measuring and testing a tennis ball to determine if the ball meets standards of size, weight, and resilience comprising
  (a) a preconditioning station having in turn a plurality of substations for flexing the ball along a variety of axes in a repeating manner;
  (b) a sizing station to determine if the diameter of the ball is too large or too small;
  (c) a weigh station;
  (d) a bounce station in which the ball is dropped against a planar and rebounds to an elevated height and the height of the bounce is compared with selected minimum and maximum heights below and above the ball,s elevated height;
  (e) compression station in which the ball is compressed under selected forces for selected times and in which deformation the ball is measured at selected times; and
  (f) indexing transport means for moving the ball in indexing fashion through the preconditioning station to and through subsequent stations in a timed systematic manner.

7. Apparatus for conditioning, measuring and testing a tennis ball to determine if the ball meets standards of size, weight, and resilience comprising:
  (a) a preconditioning station having in turn a plurality of substations for flexing the ball along a variety of axes in a repeating manner;
  (b) a sizing station to determined if the diameter of the ball is too large or too small;
  (c) a weigh station;
  (d) a bounce station in which the ball is dropped against a planar and rebounds to an elevated height and the height of the bounce is compared with selected minimum and maximum heights below and above the ball,s elevated height;
  (e) a compression station in which the ball is compressed under selected forces for selected times and in which deformation the ball is measured at selected times; and
  (f) indexing transport means for moving the ball in indexing fashion through the preconditioning station to and through subsequent stations in a timed systematic manner,
  wherein the position of the tennis ball after being dropped and having rebounded is determined to measure the angle of the ball's bounce with respect to such planar surface.

* * * * *

UNITED STATES PATENT AND TRADEMARK OFFICE
CERTIFICATE OF CORRECTION

PATENT NO.  : 4,876,658

DATED       : October 24, 1989

INVENTOR(S) : HASS

Page 1 of 3

It is certified that error appears in the above-identified patent and that said Letters Patent is hereby corrected as shown below:

```
Column 1, line 60, "FIG." should read --FIG. 1;--.
Column 2, line 10, "13 D" should read --13D--.
Column 2, line 28, " Fig. IB" should read --FIG 1B--.
Column 2, line 39, "as language" should read --assembly
      language--.
Column 2, line 40, "Appendices 1 -" should read --Appendices
1-4--.
Column 2, line 46, "The ball" should read --"..The' ball--.
Column 2, line 47, "eights" should read --eighths--.
Column 2, line 48, "(6.67 cm).)" should read --(6.67 cm.)--.
Column 2, line 54, "...The" should read --The--.
Column 2, line 62, A new paragraph should begin with
      "Regulations".
```

UNITED STATES PATENT AND TRADEMARK OFFICE
CERTIFICATE OF CORRECTION

PATENT NO. : 4,876,658

DATED : October 24, 1989

INVENTOR(S) : HASS

It is certified that error appears in the above-identified patent and that said Letters Patent is hereby corrected as shown below:

```
Column 3, line 4,  "keyhole" should read --keyhole-shaped--.
Column 3, line 5,  "rotated n" should read --rotated in--.
Column 3, line 14, "sinoe" should read --since--.
Column 3, line 36, "115y" should read --15y--.
Column 3, line 46, "weem" should read --ween-.
Column 3, line 61, "63b" should read -63a, 63b--.
Column 4, line 32, "83aare" should read --83a are--.
Column 5, line 2,  "108 aand" should read --108a and--.
Column 5, line 7,  "1107 a" should read --107a--.
Column 5, line 57, "T," should read --T0--.
Column 5, line 59, "Time" should read --time--.
Column 5, line 60, "FIG/11A" should read --FIG. 11A--.
Column 5, line 60, "Time" should read --time--.
Column 5, line 63, "computers" should read --computer's--.
Column 5, line 64, "(FIG. 1B )" should read --(FIG. 1B)--.
Column 5, line 64, "Time" should read --time--.
Column 6, line 8,  "xx'" should read --x'--.
Column 6, line 9,  "substation y", should read --substation y'--.
Column 6, line 35, "t In" should read --In--.
Column 6, line 35, A new paragraph should begin with "In FIGS"
Column 7, line 13, "LEDI" should read --"LED1--.
Column 7, line 30, "74LSII" should read --74LS11--.
Column 7, line 36, "side,," should read --side,--.
```

UNITED STATES PATENT AND TRADEMARK OFFICE
CERTIFICATE OF CORRECTION

PATENT NO. : 4,876,658

DATED : October 24, 1989

INVENTOR(S) : HASS

It is certified that error appears in the above-identified patent and that said Letters Patent is hereby corrected as shown below:

```
Column 7, line 41, "FIG.." should read --FIG.--.
Column 7, line 45 "-8" should read --8--.
Column 7, line 67, A new paragraph should begin with "The three"
Column 8, line 1, "UllIA" should read --UllA--.
Column 8, line 2 "UIIA" should read --UllA--.
Column 8, lines 2, 3, Delete additional space between "lines" and
     "LB0-LB2".
Column 8, line 16 "OCI" should read --OCl--.
Column 8, line 20, "30 solid" should read --solid--.
Column 8, line 20 "SSR ," should read --SSR∅,--.
Column 8, lines 19, 20, Delete additional space between "to" and
     "solid".
Column 8, line 37, "station;" should read --station; and--.
Column 8, line 65, "means;" should read --means; and--.
Column 9, line 1, "whereby" should begin a new line.
Column 9, line 27, "ball,s" should read --ball's--.
Column 10, line 18, "ball,s" should read --ball's--.
```

Signed and Sealed this

Fourteenth Day of January, 1992

Attest:

HARRY F. MANBECK, JR.

*Attesting Officer*   *Commissioner of Patents and Trademarks*